(12) United States Patent
Filippini et al.

(10) Patent No.: US 7,092,089 B2
(45) Date of Patent: Aug. 15, 2006

(54) METHOD AND SYSTEM FOR CHEMICAL OR BIOCHEMICAL ANALYSIS OF A TARGET ANALYTE IN A TARGET ENVIRONMENT

(75) Inventors: Daniel Filippini, Linköping (SE); Ingemar Lundström, Linköping (SE)

(73) Assignee: RGB Technologies AB, Stockholm (SE)

( * ) Notice: Subject to any disclaimer, the term of this patent is extended or adjusted under 35 U.S.C. 154(b) by 0 days.

(21) Appl. No.: 10/501,935

(22) PCT Filed: Feb. 7, 2002

(86) PCT No.: PCT/SE02/00207

§ 371 (c)(1),
(2), (4) Date: Jul. 21, 2004

(87) PCT Pub. No.: WO03/067936

PCT Pub. Date: Aug. 14, 2003

(65) Prior Publication Data

US 2005/0052652 A1 Mar. 10, 2005

(51) Int. Cl.
*G01J 3/10* (2006.01)
*G01J 3/18* (2006.01)

(52) U.S. Cl. .................................. 356/328; 356/402

(58) Field of Classification Search ................ 356/308, 356/309, 319–328
See application file for complete search history.

(56) References Cited

U.S. PATENT DOCUMENTS

| 2,793,560 | A | * | 5/1957 | Rennick ..................... 356/308 |
| 3,561,872 | A | * | 2/1971 | Grabowski et al. ......... 356/309 |
| 4,875,771 | A | | 10/1989 | Bowley et al. |
| 5,372,502 | A | | 12/1994 | Massen et al. |
| 5,386,112 | A | | 1/1995 | Dixon |
| 5,418,614 | A | | 5/1995 | Brost et al. |

* cited by examiner

*Primary Examiner*—F. L. Evans
(74) *Attorney, Agent, or Firm*—Venable LLP; Eric J. Franklin (57) ABSTRACT

This invention relates to a practical low cost method and devices which exploits the benefits of several photo-assisted analytical techniques involving controlled light sources. The method comprise the use of a program controlled display (like computer, mobile telephones to TV screens) used as a light source for illuminating a detector specially suited to capture the light interaction with a test environment, allowing to generate distinctive spectra and chemical or biochemical images of the environment. Additionally, the information can be acquired in situ but immediately analyzed on line via internet.

29 Claims, 10 Drawing Sheets

METHOD AND SYSTEM FOR CHEMICAL OR BIOCHEMICAL ANALYSIS OF A TARGET ANALYTE IN A TARGET ENVIRONMENT

BACKGROUND OF THE INVENTION

There is a broad range of analytical techniques which rely on light interaction with a particular medium, as for example visible absorption spectroscopy (VIS spectroscopy), surface photovoltage spectroscopy (SPS), or scanning light pulse techniques (SLPT or LAPS) used in chemical or biochemical sensing.

All of them provide useful and complementary information of the target environment (hereinafter sometimes referred to as an "analyte") but due to the complexity of the systems, which are mainly related to the requirements for the light sources, their extension to practical applications is hampered, being in general confined to expensively furnished laboratories or to devices dedicated for specific purposes.

The complexity and sophistication of the involved light sources comprised in these experiments, relate to the optical components and the controlled micro-positioning required to direct the monochromatized light through the output slit.

The objective of the present invention is to provide a practical low cost method and associated devices which supplies micro-positioning, monochromatization and intensity modulation allowing to exploit benefits from the above mentioned techniques and others requiring precisely controlled light sources.

The invented method in general terms, consists of the use of a program controlled display (like computer monitors, mobile telephones or TV screens) as a light source. The mechanical positioning is substituted by the ability of the screen to sequentially illuminate contiguous pixels, precisely and regularly patterned in any of the different alluded displays. Instead of a monochromator this same accurate positioning can be used to monochromatize light using a illuminated region on the screen as a mobile light source in front of a fixed diffractive element specially placed in front of the light.

Additionally, different RGB colors just sequentially displayed in the screen provide a light source suitable with spectral response measurements, which is a main goal for colorimetric sensing approaches. Furthermore the different pixels in the light source can be individually programmed with respect to color and intensity. Through the use of a lens between the light source and the test object also small test objects can be illuminated. The use of a program controlled display as a light source makes it also possible to scan the light over the test object.

The use of detectors like digital cameras, video and web cameras is thus one interesting possibility.

The invention allows for instance simplified illumination of a test sample and/or detector specially designed to be affected by a target environment. In this respect already developed indicator materials or molecules for optical detection using normal (monochromatic) light sources can be used. It is also the possibility to develop indicators which are optimized to be used together with rgb-colors.

Additionally, the information can be processed in situ by the user or only acquired in situ but analyzed on line through an internet connection, where expert interpretation can be supplied.

The general inventive principle mentioned above, has particular characteristics depending on the considered analytical technique that is to be emulated.

For instance, in the case of VIS spectroscopy, the standard technique requires a visible light source, a monochromator, a chopper and a detector.

Figure 1:
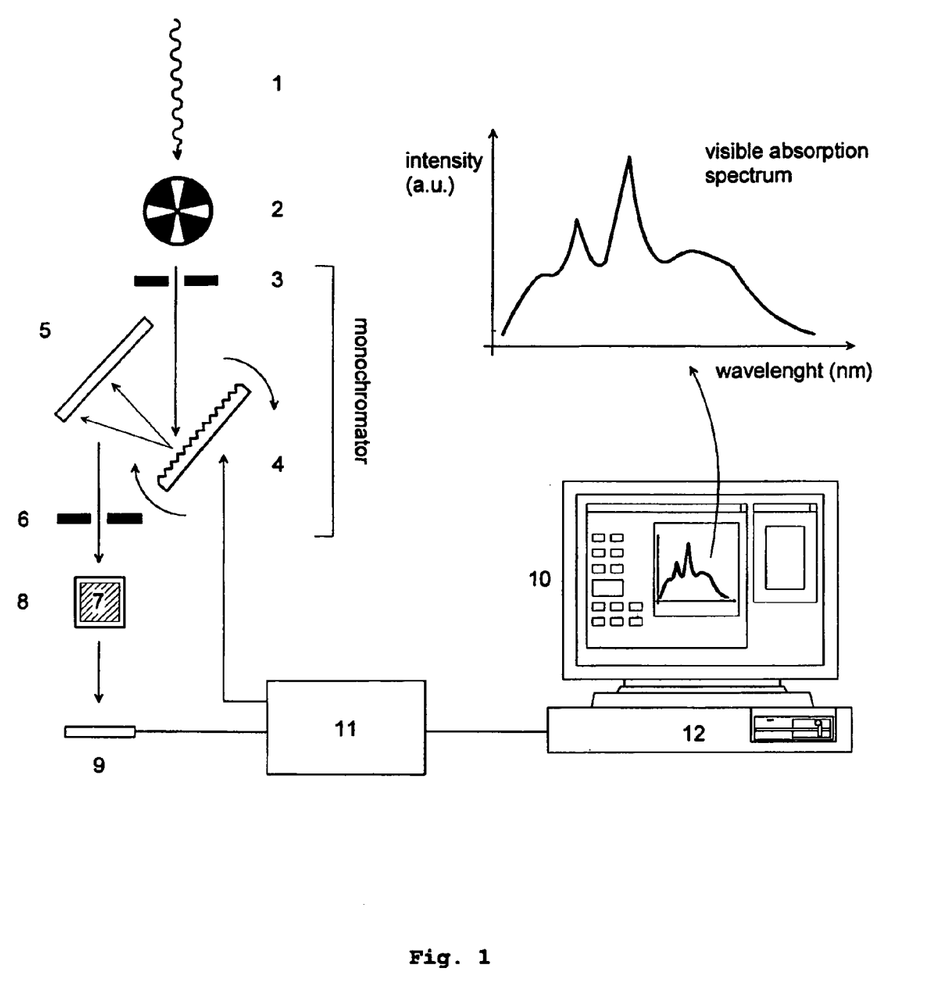
FIG. 1. depicts a standard visible absorption spectroscopy setup.

The monochromatized light, with a narrow spectral width determined by the monochromator slit width, is passed through a transparent cuvette where the sample substance is placed, in this case a liquid, and the emerging light is captured in a detector. Depending on the detector requirements a light chopper can be interposed in the light path (FIG. 1).

The VIS absorbing properties of different materials depend on their composition, and by the introduction of chemical agents (like chromophores or fluorescent labels) a large amount of chemical or biochemical properties can be traced and selectively identified through their spectral response.

The principle is not only limited to liquids, but also absorbing solids, gels or polymers like labeled DNA array slides or gas sensitive polymers can be analyzed.

Spectra acquisition requires a computer controlled system able to coordinate the supplied wavelength and this minimally comprises a programmable monochromator constraining the technique to laboratories.

In the case of SPS, or similar techniques used in semiconductor interface analysis like electric field induced SPS (EFISPS) or internal photoemission spectroscopy (IPE), the main principle is to excite carriers in semiconductor structures which are illuminated at a particular wavelength. The spectral range to scan depends on the semiconductor band gap but also sub-band gap energies can provide information of surface states.

Figure 2:
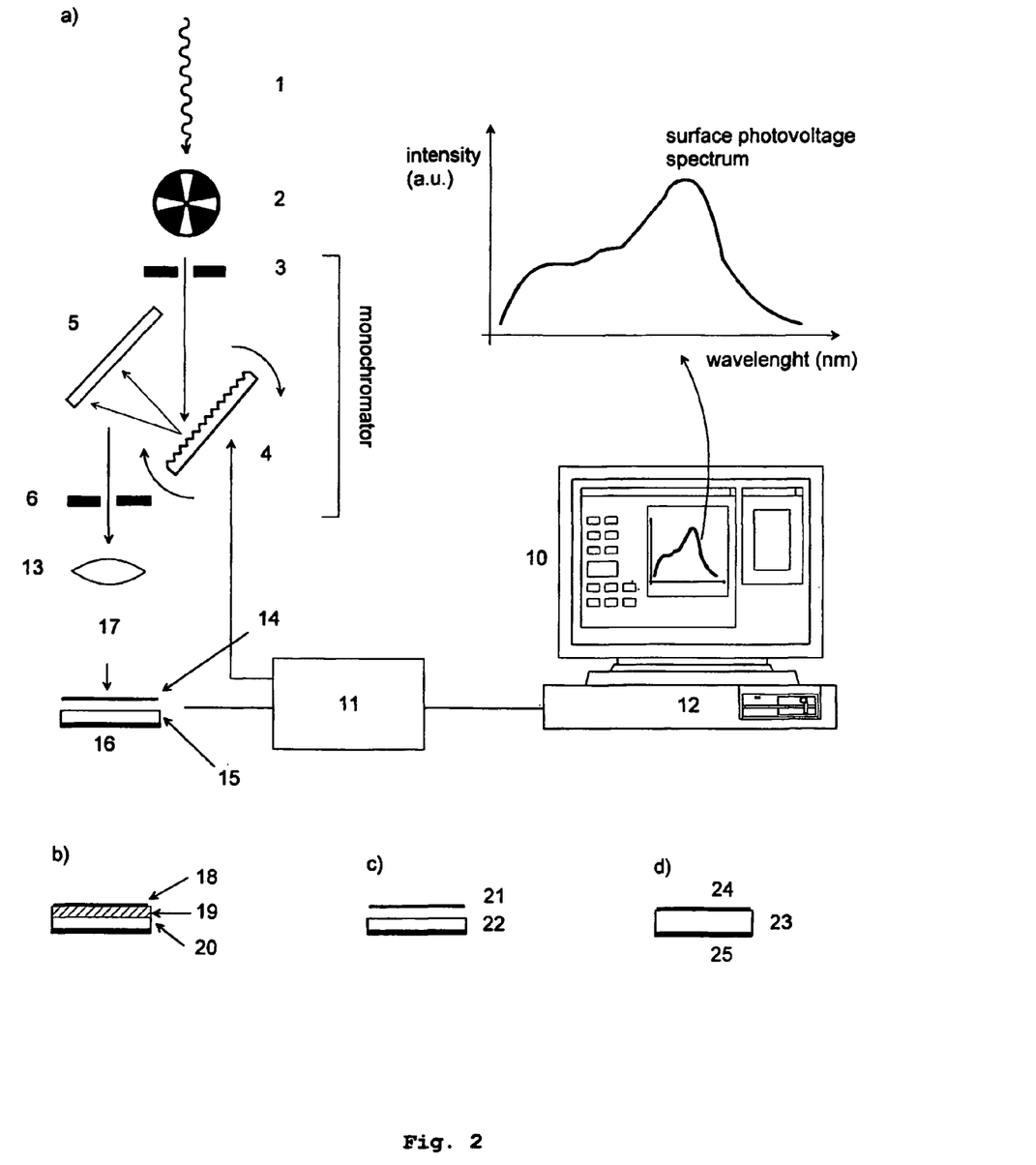
FIG. 2. a standard surface photovoltage spectroscopy setup.

In SPS, a focused monochromatic light beam is used to illuminate the semiconductor substrate at a controlled chopping frequency, which provides transient photocurrents related to surface or interface states (a complete review of SPS and related techniques can be found in L. Kronik, Y. Shapira, *Surf. Sci. Reports* 37, 1–206 (1999)). The technique, can be adapted for sensing applications, but still requires an expensive controlled light source (FIG. 2).

Figure 3:
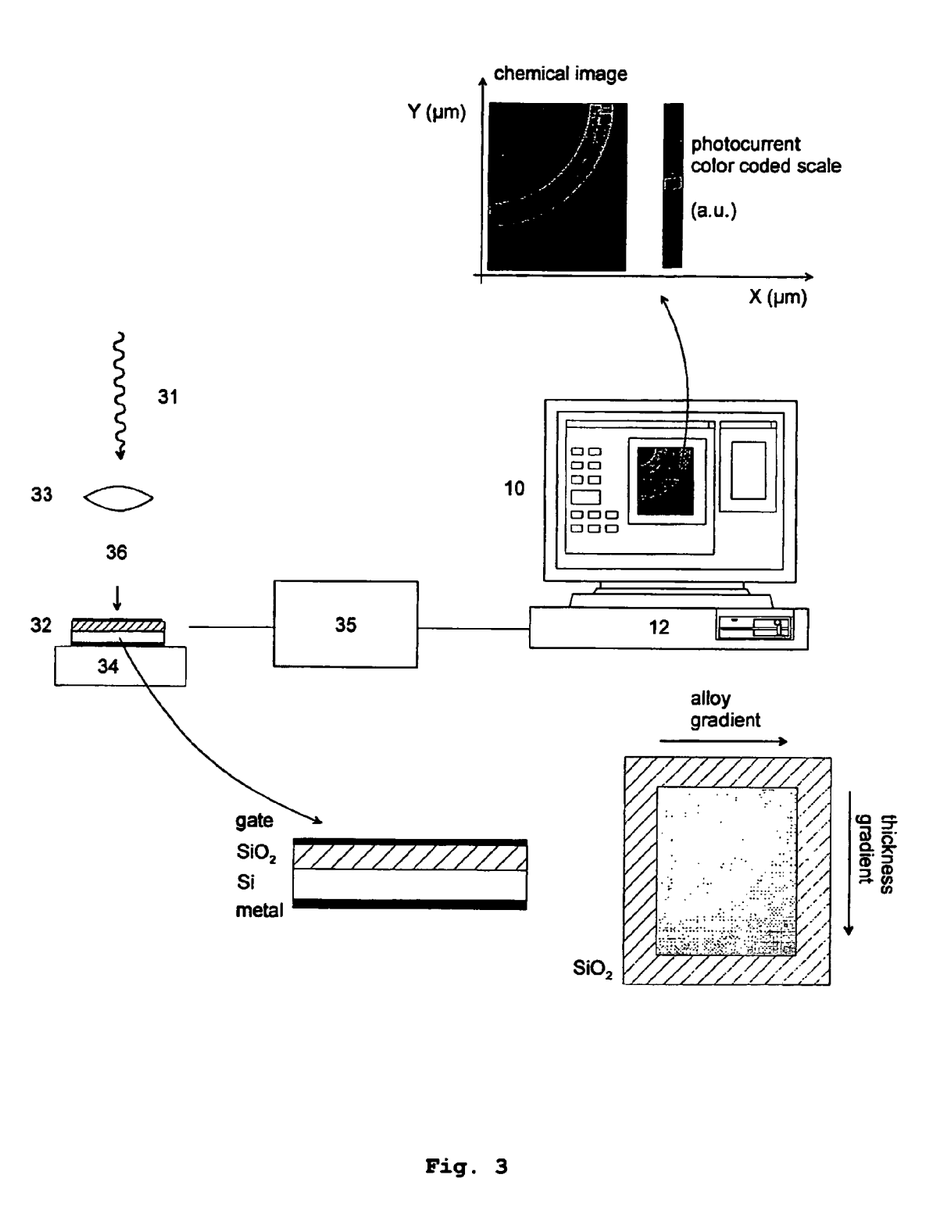
FIG. 3. a standard scanning light pulse technique (SLPT) setup.

If the light beam or a laser beam is scanned over the semiconductor, a spatially resolved map of the interface properties can be composed in the so called SLPT techniques (I. Lundström, et al., *Nature* 352, 47–50 (1991)). Providing chemically sensitive biasing electrodes of different materials and thicknesses spatially distributed the technique provides selective chemical images to gas mixtures and odors (FIG. 3).

If the biasing electrode is replaced by an electrolyte the device becomes a powerful potentiometric tool for chemical or biochemical analysis known as light addressable potentiometric sensor (LAPS, D. Hafeman, et al., *Science* 240, 1182–1185 (1988)).

In many of these approaches again, there are complex elements as micropositioned modulated laser beams with the associated focusing optics which makes field applications impracticable.

SUMMARY OF THE INVENTION

The object of the invention is achieved in a simple way by replacing the complex illuminating systems by a screen or display commanded by software.

In this way the display already used to visualize results and to provide a user interface required in all of these computerized techniques, may become a large area light source with configurable properties able to supply all the techniques simultaneously. According to one embodiment, a color, size, shape, modulation and background color of an illuminating area are configured through a user interface.

Firstly analyzing the VIS spectroscopy, if we consider that for many applications what is required from a spectrum is just its fingerprint capacity to identify a particular analyte, this is achievable by successively displaying RGB colors (color scanning) in a region of the display used as light source.

For instance, a cathode-ray tube (CRT) computer monitor, from the point of view of our goals, is a light source where a sweeping electron beam, excites a matrix of phosphorous dots which coat the screen on its inner side.

Figure 4:
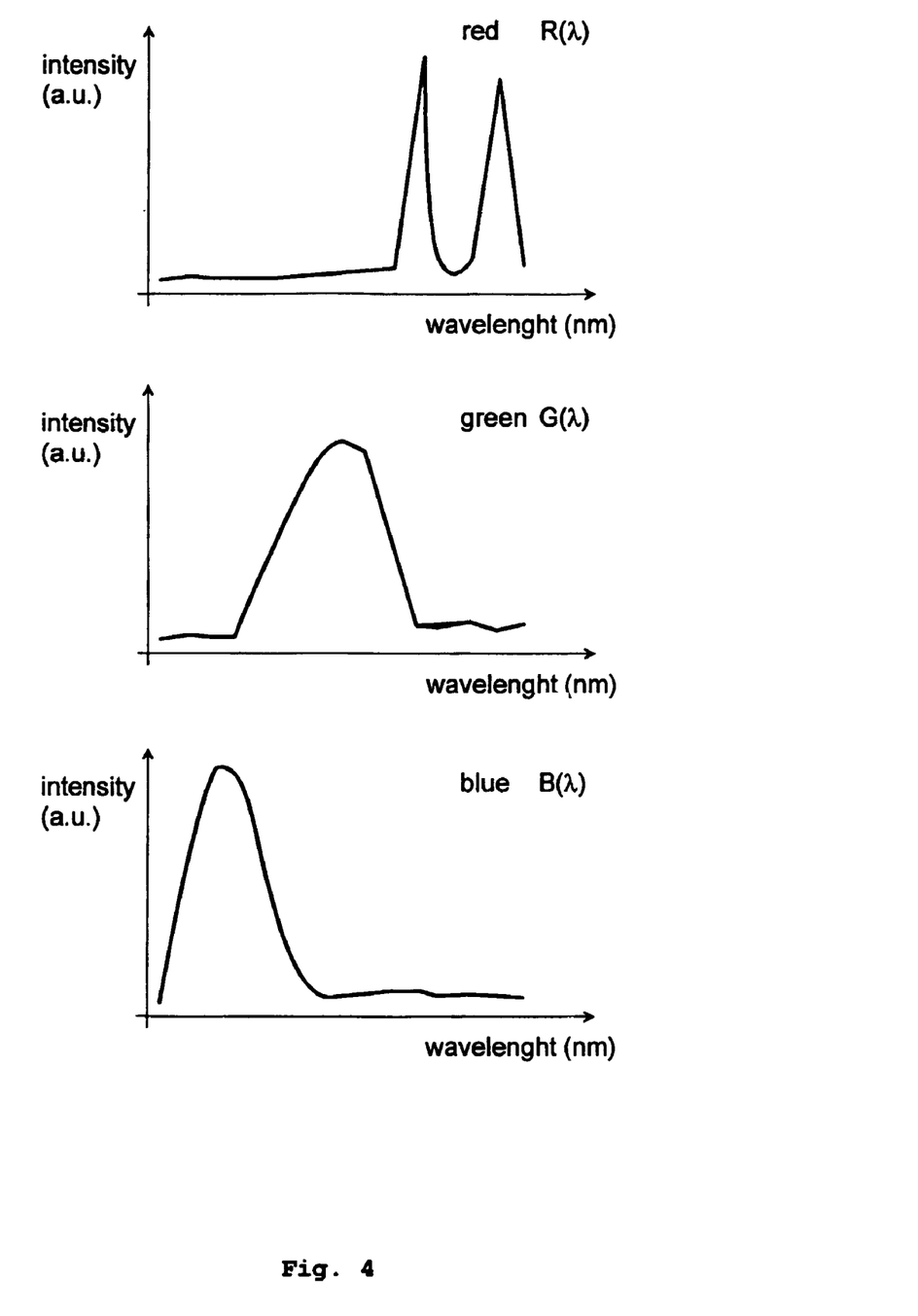
FIG. 4. typical spectral distribution of the different RGB color spots in one pixel of a CRT screen.

Phosphorous materials are chemicals which emit light when excited by a stream of electrons, and different phosphorous materials emit differently colored light. In the case of CRT color monitors each dot in the screen consist of three blobs of blue, red and green emitting phosphors, which make up what is known as a single pixel. Different intensities of each color can create the illusion (for the human eye) of many different colors and within a broad range of intensities. Actually each individual color (red, green and blue) does not consist of a monochromatic source but a particular intensity distribution instead ($R(\lambda), G(\lambda)$ and $B(\lambda)$ as illustrated in FIG. 4). What is emitted from the display is the sum of individual spectra weighted by r, g and b values individually ranging from 0 to 1 (0 to 255 for the individual rgb channels of a 24 bits video card):

Emitted color$(\lambda) = r \times R(\lambda) + g \times G(\lambda) + b \times B(\lambda)$ The combination of different possible rgb values provides a range of circa 16 millions of colors. If a set of rgb colors is arbitrarily chosen to imitate the visible spectrum perception, the emitted spectra are like those indicated in FIG. 5

Figure 6:
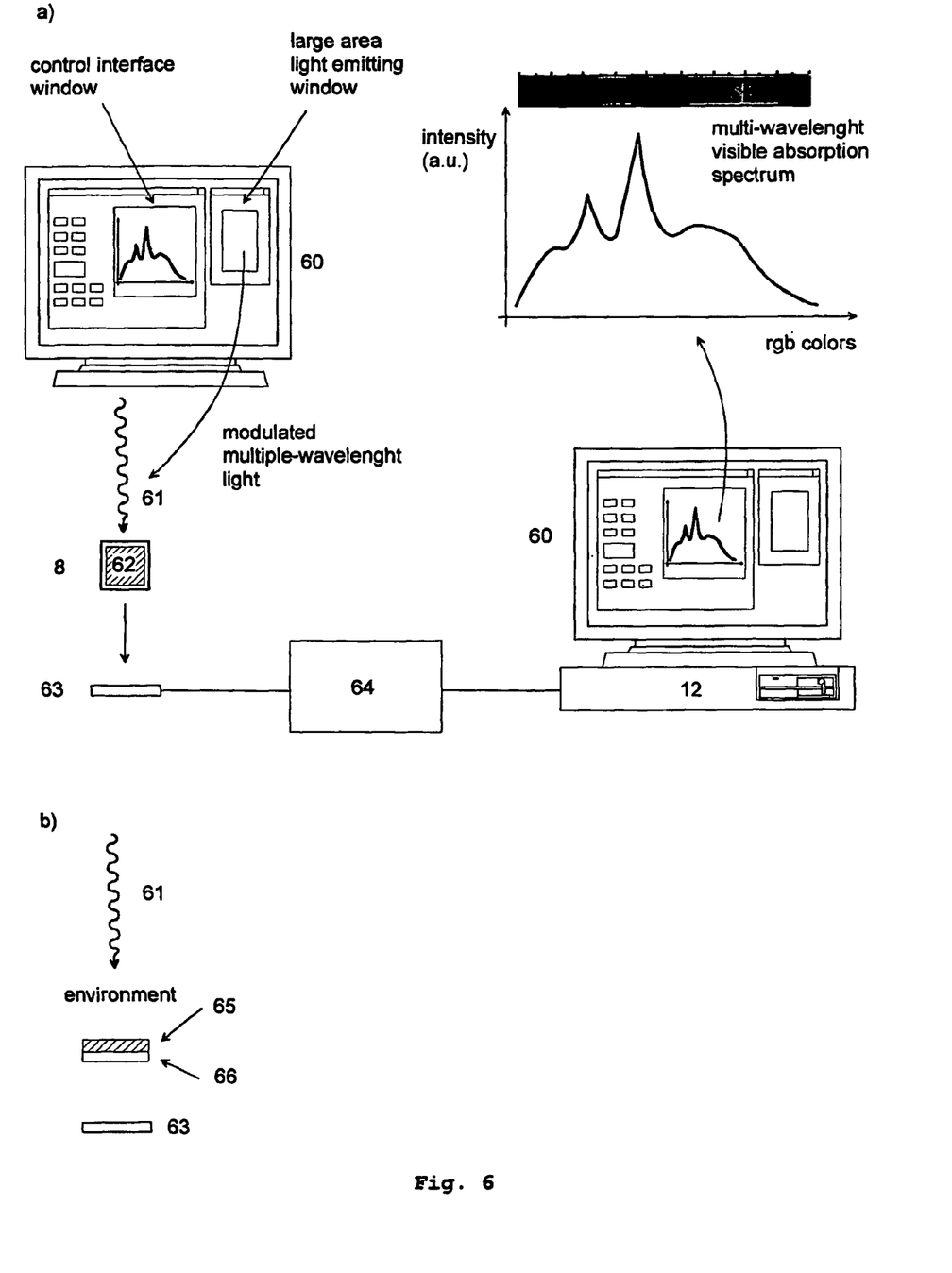
FIG. 6. screen assisted VIS spectroscopy.

This set can be used to perform multi-wavelength color scanning retaining the ability to generate distinctive absorption spectra (FIG. 6).

In FIG. 6 the test sample can be either a liquid contained in a cuvette or a material on a transparent substrate reacting on target species in the test environment. Numerous indicator systems for the detection of dissolved and gaseous species have already been developed (for instance for biosensing applications in R. Jelinek, S. Kolusheva, *Biotechnology advances* 19, 109–118 (2001), vapor sensitive porphyrines in N. Rakow, K. Suslick, *Science* 406, 710–713 (2000)). Many of them are applicable in the present invention without modification. We envisage, however, the possibility to develop indicators optimized for the use of rgb-based colors. In the first implementation of the invention it consists of the programmable light source (monitor, display, mobile phone, TV-screen), which provides a controlled sequence of rgb colors, a test sample (a liquid or a solid-like material) designed to change its spectral response in the presence of an analyte to be detected (hormones, toxins, environmental pollutants, poisonous gases, etc.), and a light detector. Not discussed but obvious is also the necessity to provide means of bringing the test environment in contact with the sample.

In this new approach the monochromator is completely replaced by an easily available system without mobile parts which also provides an intrinsic chopping intensity required for some types of light detectors.

This is because, once excited by the electron beam the pixel intensity decays until the next time the beam reaches it in its scanning cycle. For a typical pixel frequency (also called refresh frequency) of 85 Hz, this constitutes an intrinsic chopping frequency for an individual pixel light source.

Larger light sources and higher total light fluxes on the sample can be produced by exiting groups of several pixels. The light from the sample can be focussed into the detector to increase the intensity on each pixel of the detector. Continuous horizontal pixels are excited with a delay of ~14 ns for a 1024×648 pixels resolution, and continuous vertical ones each ~14 μs (~71 kHz), but the 85 Hz chopping patterns are dominating compared with the high frequency superposition.

Regarding the detectors, these can be of different types, like large area metal-oxide-semiconductor devices, digital or video cameras, polymer photo-detectors or conductive photo-sensitive sensors which depending on the particular application can be patterned on a flexible or rigid substrate. Regarding the optical properties of the sample substance not only light absorption but also fluorescence is possible to monitor.

When a liquid crystal display (LCD) monitor is used instead of a CRT, the refresh frequency has a different meaning. In this kind of screens each pixel intensity remains constant until the next scanning cycle cause a change or not depending on the information that is to be displayed. If the detector requires a chopped light source, this can be introduced by switching on and off the illuminated region in each refresh cycle. Of course this approach is also suitable to CRT screens if excitation frequencies lower than the refresh frequency are required.

The case of surface photovoltage spectroscopies follows the same considerations given above but there is also chemical or biochemical interaction with the sensing device in addition to the absorption that may occur. These devices can e.g. be semiconductor samples with transparent electrodes (e.g. indium thin oxide—ITO), metal-insulator-semiconductor (MIS) structures, suspended gate MIS devices or electrochemical sensors, where the interaction with the analyte also changes the electrical properties of the light detector itself.

The light source can be reduced to an individual pixel, still preserving the light properties already described, with sizes around 250 μm by side and scanning pitch in the same range. In these conditions this tiny light source (or also other composed by several illuminated pixels) can be spatially scanned over a large area sensing device in the same fashion as the standard SLPT or LAPS but eliminating expensive and complex micropositioning tables and focusing optics.

Regarding the detector itself, for this kind of application similar devices as used in the standard technique can be exploited in the display assisted version.

Also combinations of VIS spectroscopy and large area, normally spatially scanned, devices can be envisaged. For instance, DNA-chips are vehicles for the investigation of genetic information in biological samples. The DNA-chips are thus important tools for present genomics research and as well as for medical diagnosis. These chips may contain up to several thousands of individual measurement spots often covering an area of some few square centimeters. They are in general interrogated using fluorescent marked oligonucleotides, which express some particular property of the biological sample, generating a distinctive pattern in the distribution of spectral responses of the array.

Figure 7:
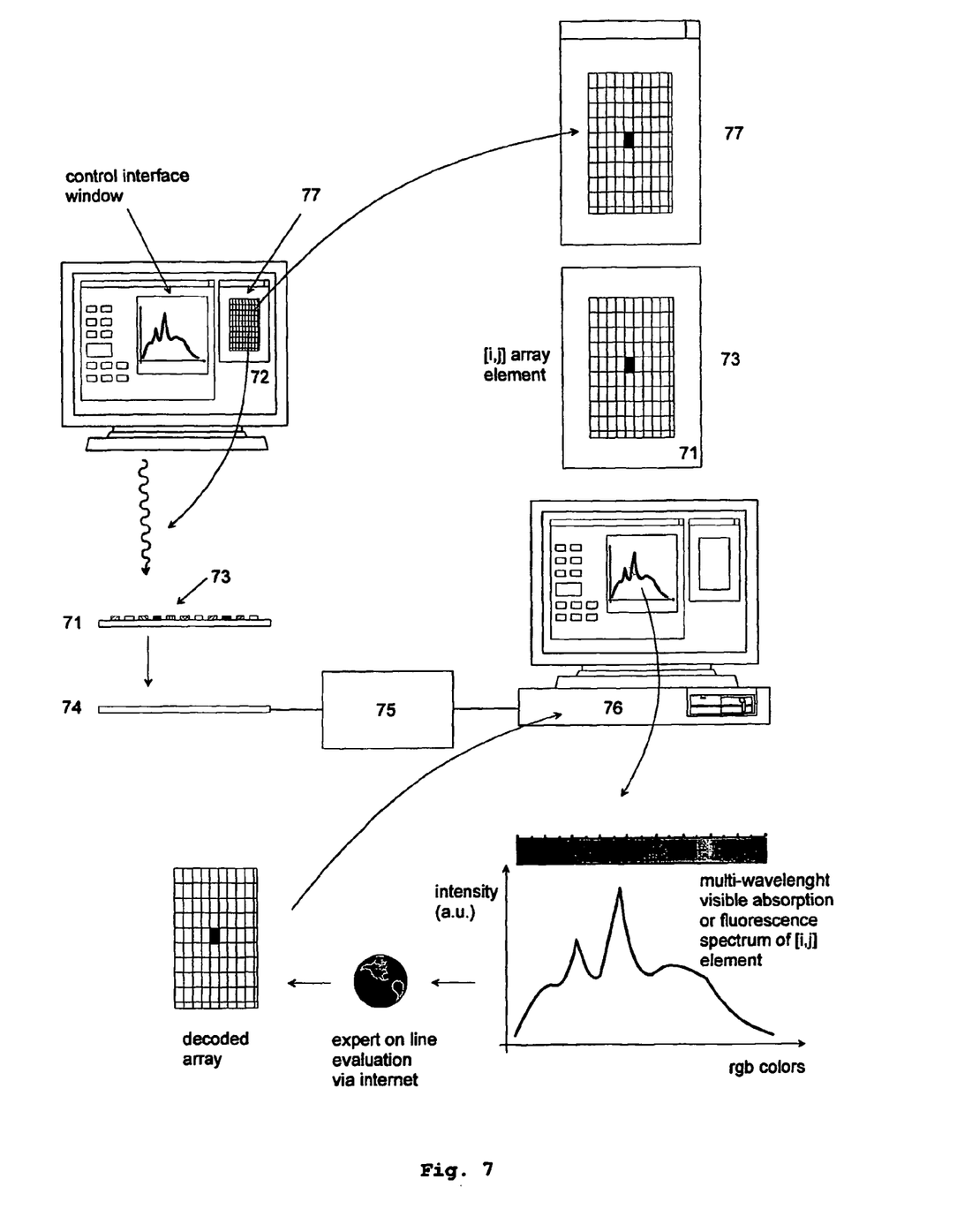
FIG. 7. screen assisted VIS spectroscopy for color identification in absorbing arrays, FIG. 8. same principle as in FIG. 7, but for the read out method using a digital video camera.

If the same concept is developed in a larger area array each individual spot, can be characterized by its spectral response without moving parts provided the positioning of multi-wavelength scanned light in front of each array element and the use of a single large area photo-detector facing the complete array (FIG. 7).

Figure 8:
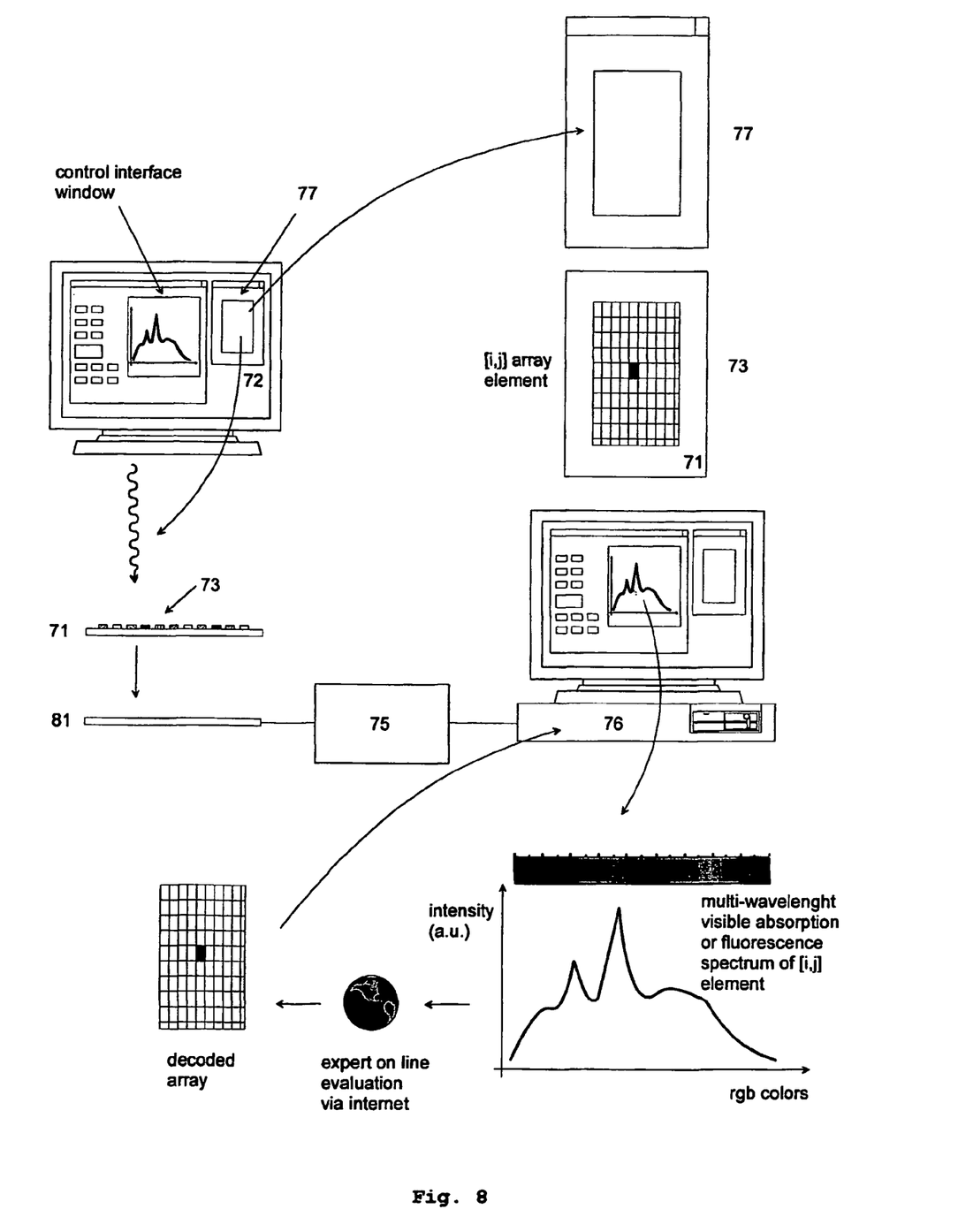

A possibility to speed up the acquisition process and also exploit already existing DNA or similar arrays is to simultaneously illuminate the complete array with a large area screen light and to acquire the collective spectra with an array light detector, like a web camera (FIG. 8).

Of course in applications, like DNA array decoding, the whole set of acquired information obtained in situ can be interpreted on line by an expert system.

As a final example, there is also the chance to obtain true monochromatic light, exploiting the positioning of the light source (a white strip on the screen for instance), by interposing a grating in the optical path, in order to expose the sample to monochromatic light. By accurately moving the light source on the screen the diffracted light is displaced on the sample. In the case of a single detector, if the diffracted light is collimated through a narrow slit, the displacement of the light source provides monochromatic light on the sample (FIG. 10).

Figure 10:
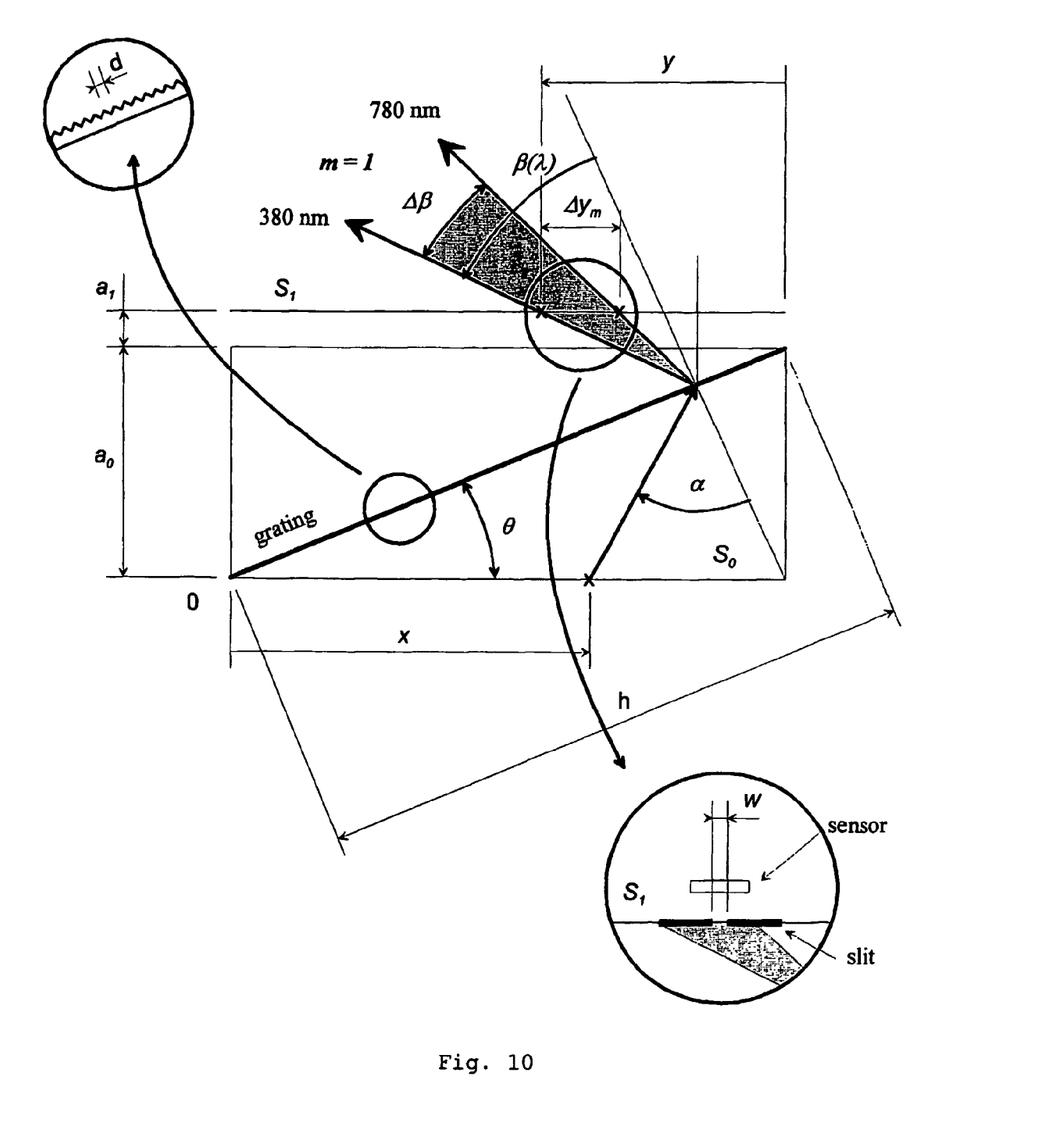

The diagram in FIG. 10 illustrates the involved variables which yields simple geometrical relations between light source displacements and resolution.

Of course in this simplified picture used to state the concept, we have omitted practical problems which similarly arises in standard monochromators, like the finite size of the source, or the compromise between the limited light intensity and the distance from the screen to enhance the color separation efficiency.

The static monochromatic is not only an example of a device working with the programmable light source, but also an approach to monochromatize light in standard SLPT setups.

In all of these examples the computer screen can be simultaneously used to display test results or for analysis of these results via software on the computer or via internet, since only a part of the screen is used as a light source in a multitasking computer platform.

It should also be pointed out that the large area light source can be focussed to a small area sample, increasing in this way the light intensity on the sample.

Figure 9:
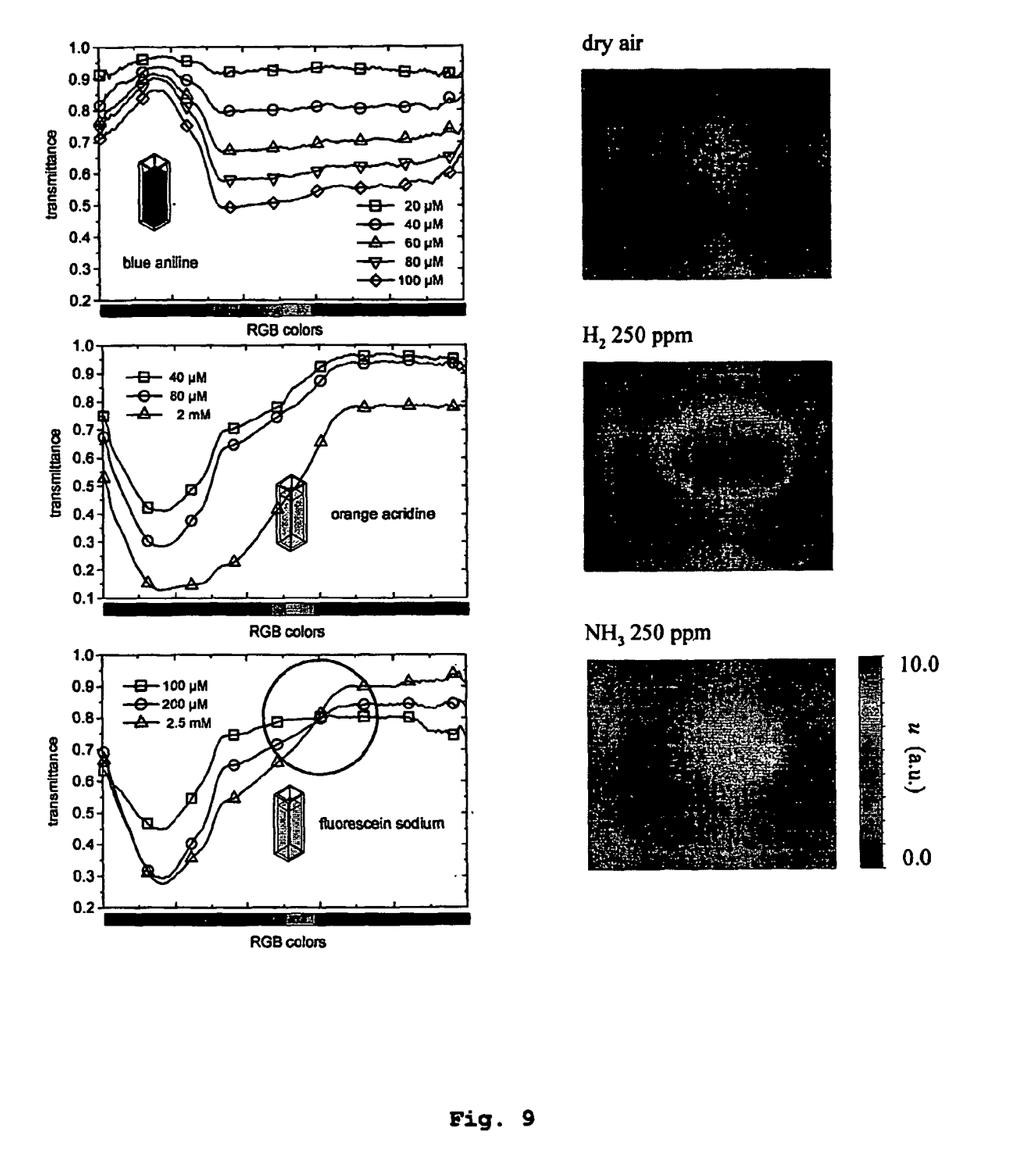
FIG. 9. screen assisted VIS absorption spectra for different liquid samples and SLPT images for different gases, and FIG. 10. static monochromator primciple.

One implementation of the invention thus consists of the use of a large area programmable light source together with a detector and a suitable designed test sample which traces the interaction with the analyte in the target environment. The test sample can be, for example, in the form of a cuvette with a suitable liquid indicator, a layer on a transparent substrate or directly the detector gate. The test sample is provided with properties necessary to detect selected species in the environment through a change in its spectral response or through its interaction with the detector, depending on the chosen mode of operation (FIG. 9).

Additionally a method and device to generate true monochromatic light is also provided.

In relation to the prior art the invented method is able to provide practical analytical applications with inexpensive and simplified versions of well established analytical techniques.

DESCRIPTION OF THE DRAWINGS

Further characteristics and advantages of the invention are apparent from the following description of the old technique as well as from the invented technique described below in conjunction with the drawings.

In the drawings.

FIG. 1. Is a standard visible absorption spectroscopy setup. A white light source 1 is monochromatized and chopped by a chopper 2 and a monochromator. The monochromator is constituted of an input slit 3, a position controlled grating 4, a mirror 5 and an output slit 6. The light leaving the monochromator passes through the test sample 7 in the cuvette 8. The emerging light is detected by a light detector 9 and its intensity displayed on a computer screen 10 as a spectrum. Via an electronic control unit 11 the computer 12 controls the position of the grating 4.

FIG. 2a. Shows a standard surface photovoltage spectroscopy setup. A white light source 1 is chopped 2, monochromatized 3–6 and then focused 13 on the semiconductor substrate 15, through the sample environment 17. The signal from the detector is coupled to a computer 12 via an electronic control unit 11, that also controls a grating 4 in the monochromator 3–6. The detector comprises a transparent vibrating electrode 14 over a semiconductor substrate 15 with a metal backside. The measured photocurrent vs. the wavelength is displayed as a diagram on the computer screen 10.

FIG. 2b. Depicts an alternative detector configuration with a transparent metal layer 18 on top of an insulating layer 19 that in turn is on top of a semiconductor layer 20. Alternatively the suspended gate detector structure of FIG. 2c can be used, where a transparent metal layer 21 is arranged suspended a short distance above a semiconductor substrate 22.

It is also possible to use the detector configuration of FIG. 2d, with a semiconductor substrate (or powder) 23 sandwiched between two electrodes 24 and 25, of which at least one is transparent.

FIG. 3. Shows a standard scanning light pulse technique (SLPT) setup. A focused chopped monochromatic light beam 31 for instance from a laser is spatially scanned over a metal-insulator-semiconductor (MIS) (alternatively over an ion sensitive device in the so called LAPS) detector 32 with a transparent metal gate, which is simultaneously exposed to the target environment 36 that is to be analyzed. The measured photocurrent is displayed on the computer screen 10 as a function of the position on the detector. The detector 32 is placed on a x-y-micropositioning table 34 and coupled to the computer 12 via an electronic device 35.

Using for instance a gate with gradients in composition and thickness, there will exist spatially distributed sensitivities and selectivities to different analytes, which are pictured as distinctive chemical images on the computer screen.

FIG. 4. Typical spectral distribution of pure red, green and blue colors displayed on a CRT screen.

Figure 5:
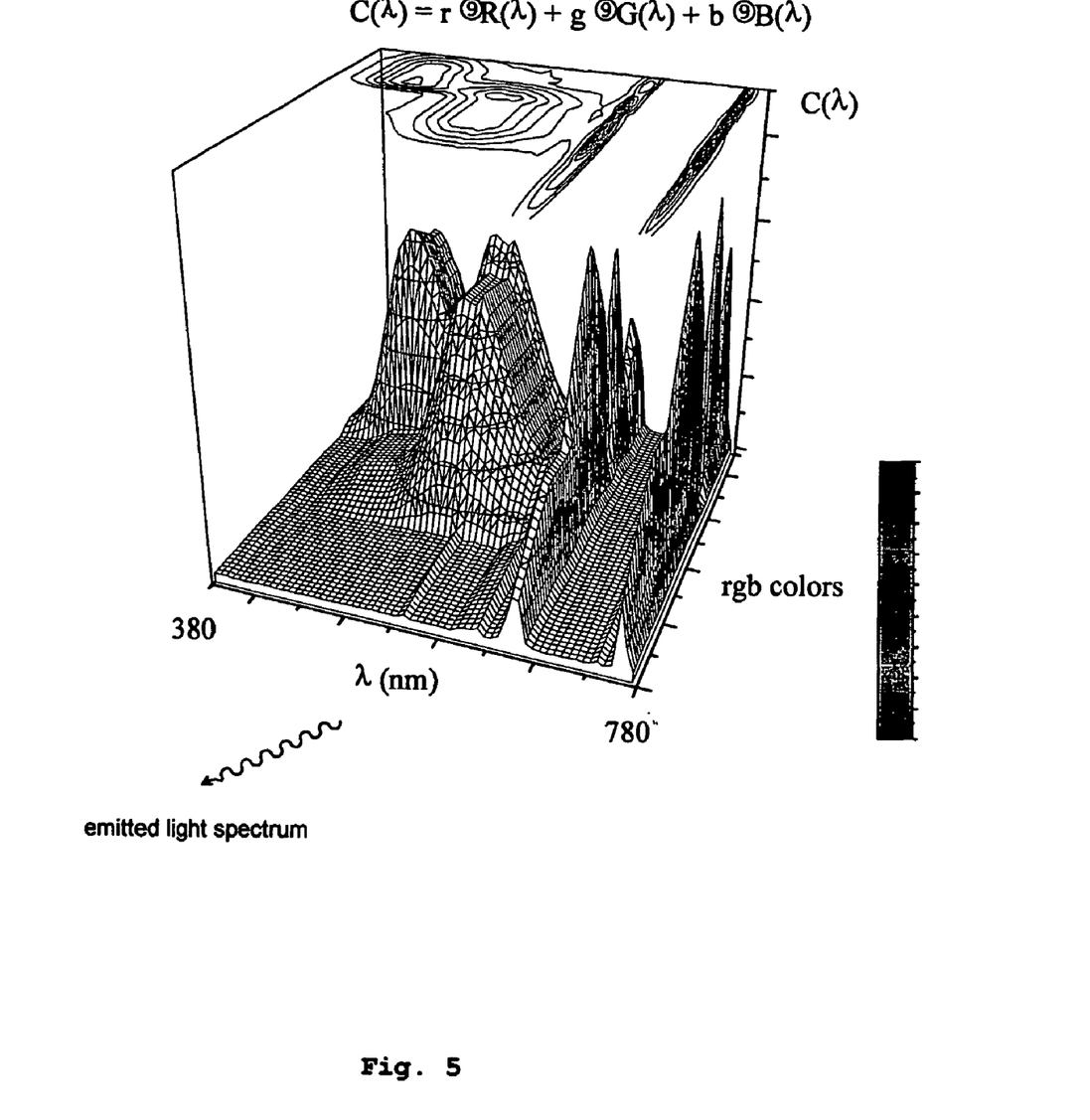
FIG. 5. spectral distribution from a CRT monitor for different R, G and B values.

FIG. 5. Typical emitted spectral distribution from a CRT monitor when different sets of rgb values are chosen to imitate the perception of the visible spectrum.

FIG. 6a. Programmed screen assisted VIS spectroscopy. The same display 60 used as control interface provides colored light 61 according to FIG. 5 which is passed through a test sample 62 and the emerging light is captured by a detector 63 coupled to the computer via a electronic device 64 plotting the resulting spectra in the same computer display. In FIG. 6b a different test sample 65 printed or deposited on a glass or polymer substrate 66, but used in the same way as in FIG. 6a is illustrated.

FIG. 7. Programmed screen assisted VIS spectroscopy for color identification of chemically sensitive arrays. The same display used as control interface provides colored light according to FIG. 5, in selected regions of the screen facing individual elements of the sample array. For instance, a glass substrate 71 is suspended on a portion of the screen 72. On this glass substrate a DNA labeled array 73 face the screen and on the other side of the substrate a single large area photodetector 74 is arranged covering the entire area of the DNA labeled array. The photodetector delivers its signals to an electronic interface 75 that delivers the signal to the computer 76. The screen under the glass substrate constitute a large area light emitting window 77, that in turn can illuminate the different elements of the array (one at time) with modulated multiple wavelength light. For each element on the glass substrate a multi-wavelength spectral response can be recorded. The resulting spectra are displayed in the same computer screen. According to one embodiment, displaying test results includes displaying a chemical or biochemical image using a photocurrent color coded scale. Expert evaluation of data and array interpretation can be provided by the computer itself or on line via internet. Additionally, if necessary it is possible to focus the light from the screen using diffractive or refractive lenses between the screen and the sample. According to one embodiment, a magnifying lens is arranged between the test sample and the detector.

The example was a DNA array but the method is applicable to any array based analysis utilizing the optical properties of the different spots of the array.

FIG. 8. Same principle as in FIG. 7, but the acquisition process is enhanced illuminating the whole sample array simultaneously and capturing the information with a detector array 81 provided by a video camera (web camera). Additionally if necessary it is possible to focus the light from the screen by using diffractive or refractive lenses between the screen and the sample, and/or between the sample and the camera. The incorporation of filters for particular applications can also be envisaged, in both FIGS. 7 and 8.

FIG. 9. VIS absorption spectra for different concentration of blue aniline, orange acridine, and fluorescent fluorescein-sodium from top to bottom on the left, and on the right SLPT images obtained using a Pt—Pd gate detector when it is exposed to dry air, hydrogen or ammonia as target environments. Note the contribution of the fluorescence to the recorded spectra in the bottom left diagram.

FIG. 10. Static monochromator principle. A point light source at a distance x from the origin 0, is displaced on the surface $S_o$ subtending a variable angle $\alpha$, with the normal of the transmission grating at a constant angle $\theta$ respect to $S_o$.

The grating pitch d and the angle $\alpha$, determines the emerging angle $\beta$ for each particular wavelength $\lambda$ at the diffraction order m. In this way the complete spectrum is decomposed along a distance $\Delta y_m$ on a surface $S_1$ at a distance $\alpha_0+\alpha_1$ from the surface $S_0$. If a collimating slit, with an slit width w, is placed on $S_1$, when the light source is displaced in x, the different components of the spectrum emerges though the slit illuminating the sensor.

If the slit is omitted there is a possibility to use an array detector in the same place and in principle obtain a full spectrum with a resolution also given by the number and size of the array detector.

The invention claimed is:

1. A method for chemical or biochemical analysis of a target analyte in a target environment, the method comprising:
    providing a test sample in or in contact with said target environment, which test sample upon interaction with said target analyte is chemically or biologically modified changing its spectral response;
    illuminating said test sample using a program controlled display as a light source, which program controlled display is composed of at least one activated pixel providing the illumination from an illuminating area of said program controlled display;
    detecting light emerging from said test sample by a detector coupled to said program controlled display, and
    displaying test results originating from signals from said detector on said program controlled display.

2. The method according to claim 1, wherein the step of providing a test sample comprises providing the test sample in the target environment.

3. The method according to claim 1, wherein the step of providing a test sample comprises providing the test sample on said detector, whereby the electrical properties of said detector upon chemical or biochemical interaction with said target analyte is affected.

4. The method according to claim 1, wherein the step of displaying test results originating from signals comprises displaying resulting spectra.

5. The method according to claim 3, wherein the step of displaying test results originating from signals comprises displaying a chemical or biochemical image using a photocurrent color coded scale.

6. The method according to claim 1, further comprising individually modulating the color of each individual pixel by software.

7. The method according to claim 1, further comprising individually modulating the light intensity of each individual pixel by software.

8. The method according to claim 1, further comprising scanning the color of each individual pixel within the visible range by software.

9. The method according to claim 1, wherein the color, size, shape, modulation and background color of said illuminating area is configured through a user interface.

10. The method according to claim 1, further comprising displacing said illuminating area of said program controlled display over time.

11. The method according to claim 1, wherein the step of displaying further comprises displaying said test results on a part of said program controlled display that is not used for illumination.

12. The method according to claim 1, further comprising placing a diffractive element between said program controlled display and said test sample.

13. The method according to claim 12, further comprising placing a collimating slit between said diffractive element and said test sample and scanning diffracted light through the collimated slit by displacement of said illuminating area.

14. The method according to claim 1, further comprising a step of evaluating said signals from said detector by software coupled to said program controlled display.

15. The method according to claim 1, further comprising a step of evaluating said signals from said detector through an on-line analysis by an expert or an expert system.

16. The method according to claim 1, further comprising controlling said program controlled display, said detector, said electronic device and said user interface by a computer.

17. A system for chemical or biochemical analysis of a target analyte in a target environment, said system comprising:
- a test sample, which, upon interaction with said target analyte is arranged to be chemically or biologically modified to change its spectral response;
- a program controlled display arranged to be used as a light source for illumination of said test sample and to be used for displaying test results, and
- a detector arranged to detect light emerging from said test sample and coupled to said program controlled display.

18. The system according to claim 17, wherein said program controlled display is a cathode ray tube computer monitor or a liquid crystal display monitor.

19. The system according to claim 17, wherein said test sample comprises molecules or materials specifically designed to show spectral changes upon chemical or biochemical reactions.

20. The system according to claim 17, wherein said test sample comprises molecules or materials specifically designed to be used together with rgb-illumination.

21. The system according to claim 17, wherein said test sample is an indicator deposited as a layer on a transparent substrate, in a cuvette or in a cavity of an analysis plate.

22. The system according to claim 17, wherein said test sample is a detector gate.

23. The system according to claim 17, wherein said detector is a web camera, a digital camera or a video camera.

24. A The system according to claim 17, wherein said detector is a semiconductor device, a conductive photo-sensitive detector, a polymer photo-detector or an ion-sensitive device.

25. The system according to claim 17, further comprising a holder for holding said test sample at a distance from said program controlled display.

26. The system according to claim 17, further comprising a magnifying lens between said test sample and said detector.

27. The system according to claim 17, further comprising a diffractive element arranged to be placed between said program controlled display and said test sample.

28. The system according to claim 27, further comprising a collimating slit arranged to be placed between said diffractive element and said test sample.

29. The system according to claim 17, further comprising a focusing lens between said program controlled display and said test sample.

* * * * *